(12) United States Patent
Rehkopf (10) Patent No.: US 10,517,308 B2
(45) Date of Patent: Dec. 31, 2019

(54) PROCESSING OF AGRICULTURAL PRODUCTS USING RADIOFREQUENCY

(71) Applicant: Ziel Equipment, Sales and Services, LLC, San Francisco, CA (US)

(72) Inventor: Andre Rehkopf, Sacramento, CA (US)

(73) Assignee: Ziel Equipment, Sales and Services, LLC, San Francisco, CA (US)

( * ) Notice: Subject to any disclaimer, the term of this patent is extended or adjusted under 35 U.S.C. 154(b) by 0 days.

(21) Appl. No.: 15/784,003

(22) Filed: Oct. 13, 2017

(65) Prior Publication Data

US 2018/0103662 A1 Apr. 19, 2018

Related U.S. Application Data

(60) Provisional application No. 62/408,661, filed on Oct. 14, 2016.

(51) Int. Cl.
| | |
|---|---|
| *A23B 7/01* | (2006.01) |
| *A23L 33/105* | (2016.01) |
| *A23L 3/54* | (2006.01) |
| *A23L 3/04* | (2006.01) |
| *A23B 7/02* | (2006.01) |
| *A61K 31/352* | (2006.01) |

(Continued)

(52) U.S. Cl.
CPC .............. *A23B 7/012* (2013.01); *A23B 7/01* (2013.01); *A23B 7/02* (2013.01); *A23L 3/01* (2013.01); *A23L 3/04* (2013.01); *A23L 3/54* (2013.01); *A23L 5/20* (2016.08); *A23L 33/105* (2016.08); *A61K 31/352* (2013.01); *A23V 2002/00* (2013.01); *A23V 2300/10* (2013.01); *A23V 2300/12* (2013.01); *A23V 2300/24* (2013.01); *A61K 2236/17* (2013.01); *Y02P 60/146* (2015.11)

(58) Field of Classification Search
CPC ................ A23B 4/01–012; A23B 5/01; A23B 7/01–012; A23B 9/04; A23L 3/005; A23L 3/01; A23L 33/105; A23L 5/20; A23L 3/04; A23L 3/10; A23L 3/40; A23L 3/54; A01G 7/04; Y02P 60/146; A23V 2002/00; A23V 2300/10; A23V 2300/12; A23V 2300/24; A61K 31/352; A61K 2236/17
USPC ................ 426/244, 234, 520–523; 219/771; 422/21–23
See application file for complete search history.

(56) References Cited

U.S. PATENT DOCUMENTS 2,473,041 A * 6/1949 Urbain ..................... A23B 5/01
                                                                 219/771
2,485,660 A * 10/1949 Robertson ................. A23L 3/01
                                                                 219/772

(Continued)

OTHER PUBLICATIONS

Dolce, How to Make One ounce of Cannabis Last Twice as Long, https://medium.com/@joedolce/how-to-make-one-ounce-of-cannabis-last-twice-as-long-2a01baf7af9d (Year: 2016).*

*Primary Examiner* — Drew E Becker
(74) *Attorney, Agent, or Firm* — McCoy Russell LLP (57) ABSTRACT

A radiofrequency heating system and methods for processing agricultural products are provided herein. The method may include positioning an agricultural product between two electrode assemblies of a radiofrequency (RF) circuit, closing the RF circuit, and heating the agricultural product to a threshold temperature in greater than a threshold amount of time.

20 Claims, 4 Drawing Sheets

(51) Int. Cl.
 *A23L 5/20* (2016.01)
 *A23L 3/01* (2006.01)

(56) References Cited

U.S. PATENT DOCUMENTS

| | | | | |
|---|---|---|---|---|
| 2,761,940 | A * | 9/1956 | Mann | A23L 3/01 219/770 |
| 3,272,636 | A * | 9/1966 | Fehr | A23L 3/01 426/234 |
| 3,830,945 | A * | 8/1974 | Scharfman | A23B 5/01 426/243 |
| 3,843,813 | A * | 10/1974 | Driggs | A23B 5/005 426/241 |
| 3,945,170 | A * | 3/1976 | Brown | A23L 3/01 53/428 |
| 4,104,410 | A * | 8/1978 | Malecki | A23B 7/0053 426/399 |
| 4,296,299 | A * | 10/1981 | Stottmann | H05B 6/62 219/771 |
| 4,554,440 | A * | 11/1985 | Lee, Jr. | H05B 3/0004 219/497 |
| 4,812,609 | A * | 3/1989 | Butot | H05B 6/54 219/771 |
| 5,345,069 | A * | 9/1994 | Grindrod | B65D 77/2032 219/725 |
| 5,885,636 | A * | 3/1999 | Carville | A47J 39/02 206/499 |
| 6,119,587 | A * | 9/2000 | Ewald | A47F 10/06 426/418 |
| 6,246,040 | B1 * | 6/2001 | Gunn | H05B 6/48 219/771 |
| 6,303,166 | B1 * | 10/2001 | Kolbe | A23B 4/01 219/771 |
| 6,638,475 | B1 * | 10/2003 | Lagunas-Solar | A23L 3/01 204/164 |
| 8,973,492 | B1 * | 3/2015 | Geveke | A23B 5/0052 99/485 |
| 2004/0016744 | A1 * | 1/2004 | Ottaway | A21B 2/00 219/391 |
| 2011/0129580 | A1 * | 6/2011 | Ko | A23B 7/005 426/419 |
| 2013/0071527 | A1 * | 3/2013 | Pesce | A23L 2/02 426/234 |
| 2013/0316051 | A1 * | 11/2013 | van der Voort | H05B 6/54 426/234 |
| 2014/0330030 | A1 * | 11/2014 | Ferri | C07C 37/004 549/389 |
| 2015/0096189 | A1 * | 4/2015 | Hawes | F26B 21/08 34/474 |
| 2015/0164127 | A1 * | 6/2015 | Long | A23L 3/005 99/342 |
| 2015/0216220 | A1 * | 8/2015 | Sonder | A23L 3/005 99/358 |
| 2016/0045471 | A1 * | 2/2016 | Stodola | A61K 31/352 424/725 |
| 2016/0235109 | A1 * | 8/2016 | Cavestro | A23L 3/005 |

* cited by examiner

FIG. 3

PROCESSING OF AGRICULTURAL PRODUCTS USING RADIOFREQUENCY

CROSS REFERENCE TO RELATED APPLICATION

The current application claims priority to U.S. Provisional Patent Application No. 62/408,661, entitled "Processing of *Cannabis* using Radiofrequency," filed on Oct. 14, 2016, the contents of which is hereby incorporated by reference in its entirety for all purposes.

BACKGROUND/SUMMARY

There are many challenges presented in the agricultural industry with regards to maintaining the integrity of an agricultural product, such as an agricultural plant product. As one example, the presence of mold or yeast may cause spoilage or degradation of agricultural plant products, for example leafy vegetables and herbs, reducing shelf life and quality of the agricultural plant products. Further, certain agricultural plant products, such as *cannabis*, require a specific moisture content during processing.

*Cannabis* is a genus of a flowering plant (family: Cannabaceae) with three species: *C. sativa*, *C. indica*, and *C. ruderalis*, and several dozen strains. *Cannabis* is grown as a natural, organic, medicinal plant in green houses or outdoors, and growing *cannabis* involves a long drying process which may involve five or more days of the *cannabis* drying on the plant. In particular, current natural harvesting practices involve cutting grown *cannabis* plants, air-drying the whole plant for approximately five days at ambient temperature conditions to reach a moisture content of about 9%, as a moisture content of 9% is optimal for mechanical trimming (mechanical trimming requires approximately a 9% to 12% moisture content for effective leaf removal).

The flowering buds of the dried *cannabis* are then removed from the dried plant by hand, followed by mechanical trimming of the "sugar leaves" of the plants. The proper moisture content of the *cannabis* plants is important, as a *cannabis* product that is too dry may lead to buds that are too brittle and breaking apart, resulting in a lower quality product. On the other hand, if the moisture content is too high, the "sugar leaves" of the plant may not be mechanically removed.

During this drying process, changes in drying conditions (e.g., relative humidity, ambient temperature, seasonal weather, etc.) may result in varying moisture content of the product, causing longer drying times, and the development of yeast and mold growth may occur. Mold or yeast infections of *cannabis* in particular may lead to a significant reduction of usable crop for a grower, as in addition to spoilage issues, there are regulatory thresholds for an amount of mold or yeast that may be present in order to sell *cannabis* for medicinal purposes. For example, the state of Colorado requires *cannabis* sold to comply with a limit of less than 10,000 colony forming units per gram (CFU/g). The drying process for other agricultural plant products, such as leafy vegetables and herbs, may present similar challenges in regards to drying such agricultural plant products to a particular moisture content.

However, conventional approaches to controlling yeast and mold growth on agricultural plant products such as the use of heating, oxygen deprivation (e.g., with $CO_2$), or use of other chemicals may not deliver acceptable results or quality of the agricultural plant products. For example, heating as a disinfecting strategy may be inconsistent, as it is difficult to ensure that all of the agricultural plant product reaches a killing temperature for the yeast and mold. Additionally, oxygen deprivation may not be a successful disinfection strategy, as yeast are anaerobic organisms. Lastly, application of other chemicals to agricultural plant products may require long processing times that range from hours to days, and these chemical applications to the agricultural plant products may not successively penetrate an agricultural plant product for sufficient reduction in killing of mold and yeast.

In view of the above challenges with conventional approaches to controlling yeast and mold growth on agricultural plant products, and recognizing that there is a need, for example, in the *cannabis* industry, to reduce yeast and mold on the dried product, the inventors herein have developed an alternative approach to controlling the presence of yeast and mold on agricultural plant products, such as leafy vegetables and herbs, and in at least some examples, *cannabis*.

In one example, this alternative approach to processing agricultural plant products may include positioning agricultural plant products between two electrode assemblies of a radiofrequency (RF) circuit, closing the RF circuit, and heating the agricultural plant product to a threshold temperature in greater than a threshold amount of time. In at least one example, the agricultural plant product may be leafy vegetables. Additionally or alternatively, the agricultural plant product may be herbs. In at least one example, the agricultural plant product may be *cannabis*.

This alternative approach to processing agricultural plant products may utilize RF heating as a post-harvest kill step to reduce the population of yeast and mold on the agricultural plant products. For example, the RF heating may be utilized as a post-harvest kill step to reduce the population of yeast and mold on dried organic *cannabis* or other agricultural plant products with minimal negative impact on the chemical composition (e.g., THC content, terpenes), natural, and organoleptic composition of the product. For example, the minimal negative impact on the chemical composition may include a minimal negative impact on color, aroma, and flavor chemicals of the agricultural plant products.

This alternative approach may be used to quickly dry the agricultural plant product for improved downstream processing. Thus, RF heating may be beneficial for removing moisture quickly to shorten the drying process, reduce the time available for yeast and molds to grow, reduce the water activity, improve handling and mechanical processing, and effectively reduce the microbial load of the product. Moreover, specifically in a case with *cannabis*, the use of RF heating may achieve drying and microbial reduction benefits without a significant impact on the medicinal properties of the *cannabis*.

Further, by utilizing RF to heat the agricultural plant product, several advantages over traditional approaches to disinfecting agricultural plant products may be achieved. For example, RF heating may be energy efficient compared to other heating methods such as natural gas based systems, steam jacket systems, or electrical heating, as RF based heating penetrates the agricultural plant product, increasing a vibration of polar molecules within the product to heat it, as opposed to heating a product via conduction. Additionally, RF may be more efficient than oxygen deprivation and chemical application for killing yeast and mold. Furthermore, by heating the agricultural plant product to a threshold temperature in greater than a threshold amount of time, the technical effect of a uniform temperature throughout the RF heated agricultural plant product and drying of the product may be achieved due to both steam caused by the RF heating and the RF waves themselves being able to penetrate the agricultural plant product.

DETAILED DESCRIPTION

A system and methods for radiofrequency (RF) heating of an agricultural plant product are described herein. In some examples, the agricultural plant product may be *cannabis*. Additionally or alternatively, the agricultural plant product may include leafy vegetables. Further, in some examples, the agricultural plant product may additionally or alternatively include herbs.

Figure 1:
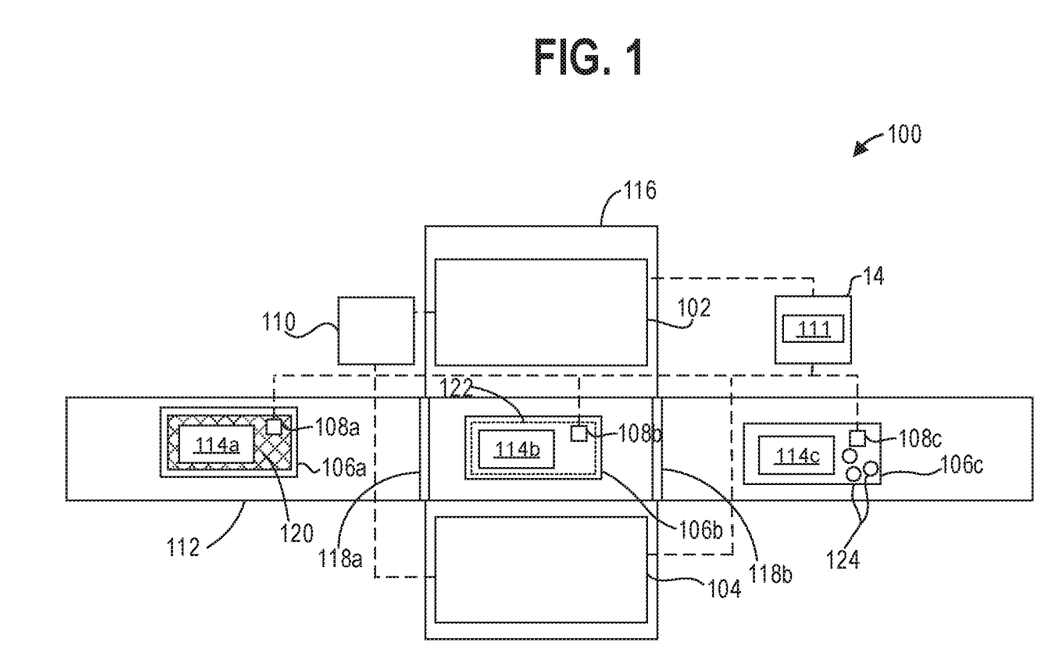
FIG. 1 shows a schematic block diagram of an example system for radiofrequency heating of an agricultural plant product

As described in FIG. 1, the system for RF heating of an agricultural plant product may include a first electrode assembly and a second electrode assembly, and an agricultural plant product may be positioned between the first electrode assembly and the second electrode assembly. The first electrode assembly and the second electrode assembly may be a part of an RF circuit, and when the RF circuit is closed, RF waves may cause heating to occur between the first electrode and the second electrode.

As also described in FIG. 1, the first electrode assembly and the second electrode assembly may be adjusted, so that the RF circuit heats the agricultural plant product to a threshold temperature in greater than a threshold amount of time. In one example, the agricultural plant product may be enclosed in a tray. The system for RF heating described herein may enable uniform heating of the agricultural product (e.g., agricultural plant products such as *cannabis*, leafy vegetables, herbs, etc.) while avoiding degradation of a chemical composition of the agricultural product. Various methods for RF heating of an agricultural plant product may be carried out with the system described in FIG. 1. For example, as described at the flow charts in FIGS. 2-4, such methods may include positioning the agricultural plant product between two electrode assemblies of a radiofrequency (RF) circuit, closing the RF circuit, and heating the agricultural plant product to a threshold temperature in greater than a threshold amount of time.

FIG. 1 shows a schematic block diagram of an example system 100 for radiofrequency heating of an agricultural plant product 114a, 114b, 114c. In some examples, the agricultural plant product may be *cannabis*. However, in other examples, other agricultural plant products may be possible, such as leafy vegetables or herbs.

The agricultural plant product 114a, 114b, 114c may be contained in enclosures 106a, 106b, and 106c, respectively. In some examples, enclosures 106a, 106b, 106c may be polycarbonate trays. In other examples, however, enclosures 106a, 106b, 106c may each comprise the same or different materials that are RF safe. Enclosures 106a, 106b, 106c may have a solid bottom in some examples. However, other shapes and forms enclosures 106a, 106b, 106c may be possible.

For example, in one example, enclosures 106a, 106b, 106c may have a mesh bottom 120 in order to allow convective air to move through the container, aiding the drying of the agricultural plant product 114a, 114b, 114c contained therein. Enclosures 106a, 106b, 106c may additionally or alternatively have a fitted lid 122 in order to aid in steam formation. Examples where enclosures 106a, 106b, 106c include a fitted lid may be advantageous for aiding the formation of steam in enclosures 106a, 106b, 106c during RF heating of the agricultural plant product 114a, 114b, 114c. The steam may be formed as RF heating causes water within the agricultural plant product 114a, 114b, 114c to increase in temperature and vaporize. This steam in enclosures 106a, 106b, 106c may aid in uniform heating of the agricultural plant product 114a, 114b, 114c, as a steam micro environment may be formed within the product itself (e.g., *cannabis* buds, leafy vegetables, herbs, etc.) as well as within enclosures 106a, 106b, 106c.

Of further benefit, this steam may be formed without adding any moisture from a foreign source and without increasing the product moisture content. Uniform heating of the agricultural plant product 114a, 114b, 114c due to the steam environment created by RF heating may help to reduce an amount of yeast and mold on the agricultural plant product 114a, 114b, 114c. For example, as the agricultural plant product 114a, 114b, 114c is being uniformly heated, a temperature of the product may be more accurately monitored, ensuring that all of the agricultural plant product 114a, 114b, 114c reaches a threshold temperature. In some examples, this threshold temperature may be a kill temperature for particular microbes such as yeast or mold.

The temperature of the agricultural plant product 114a, 114b, 114c within enclosures 106a, 106b, 106c may be detected via a temperature probe 108a, 108b, 108c. Temperature probe 108a, 108b, 108c may be a fiber optic probe that measures the temperature of the product throughout the RF heating process. In some examples, sensors may include sensors suitable for the RF environment. However, other types of temperature sensors may be possible.

In the case of *cannabis*, as one example, the temperature probe 108a, 108b, 108c may be placed within an average sized bud in order to estimate a temperature of all of the product within enclosure. A measuring tip of the temperature probe 108a, 108b, 108c may be positioned so that it penetrates the densest part of the bud in order to ensure more accurate monitoring. In examples where other leafy vegetables or herbs may be undergoing the RF heating process, however, the temperature probe 108a, 108b, 108c may be placed within an average sized unit of such leafy vegetable or herb.

The temperature probe 108a, 108b, 108c may output a signal to controller 14 indicative of a temperature of the product within the enclosure. In some examples, a plurality of temperature probes 108a, 108b, 108c may be used in order to more accurately estimate a temperature of the product within the enclosure 106. In examples where a plurality of temperature probes 108a, 108b, 108c may be used, these multiple temperature probes may be positioned within the product (e.g., multiple *cannabis* buds, leafy vegetables, herbs, etc.) and in the tray in order to detect a temperature at multiple horizontal and vertical positions.

As shown in FIG. 1, enclosure 106b containing agricultural plant product 114b and temperature probe 108b, may be positioned between a first electrode assembly 102 and a second electrode assembly 104. It is noted that the temperature probe 108b may be positioned by itself or with one or more additional temperatures in any one or more of the locations described herein.

In at least one example, the enclosure 106b may be positioned between a first electrode assembly 102 and a second electrode assembly 104 on a conveyor belt 112. For example, enclosure 106b may be moved from a position upstream of the first electrode assembly 102 and the second electrode assembly 104, such as where enclosure 106a is positioned in FIG. 1, to instead be positioned between the first electrode assembly 102 and the second electrode assembly 104. Examples where the RF heating system includes such a conveyor belt 112 may be advantageous to assist in moving the enclosures 106a, 106b, 106c that contains the agricultural plant product 114a, 114b, 114c to a position between the first electrode assembly 102 and the second electrode assembly 104 to be RF heated.

In other examples, however, there may simply be a surface (e.g., platform, table) to manually position the enclosures 106a, 106b, 106c and the agricultural plant product 114a, 114b, 114c contained respectively therein between the first electrode assembly 102 and the second electrode assembly 104.

In at least one example the first electrode assembly 102 and the second electrode assembly 104 may be contained within an RF circuit enclosure 116 to aid in directing the RF heating to the agricultural plant product contained within an enclosure 106 between the first electrode assembly 102 and the second electrode assembly 104. Such an RF circuit enclosure 116 may comprise at least one door to enable insertion and removal of agricultural plant product from between the first electrode assembly 102 and the second electrode assembly 104. For example, in a case where the RF heating system may only enable batch processing of agricultural plant product, the RF circuit enclosure may include a single door to enable manual insertion and removal of agricultural plant product between the electrode assemblies.

In a case where the RF heating system enables continuous processing of agricultural plant product, however, the RF heating system may comprise a conveyor belt 112 that extends both upstream and downstream of the first electrode assembly 102 and the second electrode assembly 104 and the conveyor belt 112 passes between the first electrode assembly 102 and the second electrode assembly 104. Thus, to accommodate the conveyor belt 112, RF circuit enclosure 116 may include a door 118a at an upstream end of the RF circuit enclosure 116 and door 118b at a downstream end of the RF circuit enclosure 116. In other examples, it may be desirable for the conveyor belt 112 to move in an uninterrupted manner. For example, when agricultural plant products are conveyed via conveyor belt 112, the RF circuit enclosure 116 may include RF suppression tunnel at an upstream end of the RF circuit enclosure 116 and a RF suppression tunnel at a downstream end of the RF circuit enclosure 116. The RF suppression tunnels allow the infeed and outfeed to move freely, while decreasing RF leakage. Such RF suppression tunnels may be used alone or in conjunction with one or more doors. When agricultural plant product is conveyed via conveyor belt 112 to position the agricultural plant product between the two electrode assemblies of the RF circuit, both doors 118a and 118b may be in an open position. Once the agricultural plant product to be processed is positioned between the two electrode assemblies, both doors 118a and 118b of the RF circuit enclosure 116 may be closed prior to closing the RF circuit for heating the agricultural plant product. Then, following the heating of the agricultural plant product, both the upstream and the downstream doors 118a and 118b may once again be opened so that the agricultural plant product that was just heated may be conveyed downstream of the RF circuit and so that any agricultural plant product positioned on the conveyor belt 112 upstream of the first electrode assembly 102 and the second electrode assembly 104. may be conveyed to a position in between the first electrode assembly 102 and the second electrode assembly 104 for subsequent RF heating.

In an additional example, when agricultural plant product is conveyed via conveyor belt 112 to position the agricultural plant product between the two electrode assemblies of the RF circuit, the agricultural plant product may be conveyed through RF suppression tunnels instead of doors 118a and 118b. In further examples, the RF suppression tunnels may be used in conjunction with either or both doors 118a and 118b.

It is noted that in at least one example, an RF heating system configured to perform continuous processing may also be utilized to perform batch processing of agricultural plant product. For example, though the RF heating system for performing continuous processing of the agricultural plant product may include some sort of conveyor to move the agricultural plant product relative to the two electrode assemblies of the RF circuit, such an RF heating system may also be used to perform batch processing of agricultural plant product. Batch processing of agricultural plant product may be carried out via the RF heating system configured to perform continuous processing by opening at least one of the doors 118a, 118b, positioning agricultural plant product between the first electrode assembly 102 and second electrode assembly 104 of the RF circuit, ensuring that both doors 118a, 118b are closed, and then closing the RF circuit. Then after the agricultural plant product has been heated to a first threshold temperature in greater than a threshold amount of time, the RF circuit may be opened, then at least one of the doors 118a, 118b may be opened, and the agricultural plant product may be manually removed from between the two electrode assemblies of the RF circuit. In some examples, RF suppression tunnels may replace or be used in conjunction with either or both doors 118a and 118b.

Further, in at least one example, one or more of the first electrode assembly 102, the second electrode assembly 104, and the conveyor belt or surface may be adjustable. Such adjustability may be advantageous to help control an intensity with which agricultural plant product positioned between the electrode assemblies are heated. For example, one or more of the first electrode assembly 102, second electrode assembly 104, and conveyor belt 112 may be adjusted prior to heating agricultural plant product via the RF circuit to ensure that the agricultural plant product is positioned relative to the electrode assemblies to heat the agricultural plant product to a threshold temperature in greater than a threshold amount of time. In such examples, it is noted that both the threshold temperature and the threshold amount of time may be predetermined based on a user input and that the positioning of one or more of the first electrode assembly 102, second electrode assembly 104, and conveyor belt 112 may adjusted to accommodate the predetermined threshold temperature and the threshold amount of time. In other examples, however, none of the first electrode assembly 102, the second electrode assembly 104, and the conveyor belt or surface may be adjustable.

In examples where one or more of the first electrode assembly 102, the second electrode assembly 104, and the conveyor belt 112 are movable in order to adjust a distance of the first electrode assembly 102 and/or the second electrode 104 from the agricultural plant product in enclosure 106, one or more of the first electrode assembly 102, the second electrode assembly 104, and the conveyor belt 112 may be movable via actuators 12 that are controllable via control system 13, and the controller 14 of control system 13 may move actuators 12 responsive to input from sensors 11 (e.g., user input sensors 111, environmental sensors, etc.).

User input sensors 111 may include one or more of capacitive touch sensors, buttons, and microphones for receiving voice commands, a mouse, keyboard, and a touch screen, for example. Other sensors that are capable of receiving a user input may also be possible.

In examples that additionally or alternatively include sensors 11, wherein the sensors 11 are environmental sensors, these environmental sensors may include one or more of temperature sensors, moisture sensors, and oxygen sensors, for example. The environmental sensors may include a temperature probe 108a, 108b, 108c, for example. However, other environmental sensors, such as moisture sensors, may also be possible.

In other examples, the first electrode assembly 102 and the second electrode assembly 104 may only be manually movable. The first electrode assembly 102 and the second electrode assembly 104 are both connected to a RF generator 110. The RF generator 110, the first electrode assembly 102, and the second electrode assembly 104 all form an RF circuit. When the RF circuit is closed, the RF generator 110 may create an alternating electric field between the first electrode assembly 102 and the second electrode assembly 104, where the agricultural plant product located in enclosure 106 is positioned. This alternating electric field between the first electrode assembly 102 and the second electrode assembly 104 causes polar molecules (e.g., $H_2O$) within the agricultural plant product to reorient rapidly due to the alternating electric field, and this rapid reorientation causes heating of the agricultural plant product due to friction of the molecules of the product as they move rapidly past one another. Thus RF heating causes heating of the agricultural plant product from within the product.

When the RF circuit is open, the RF generator 110 is unable to cause an alternating electric field between the first electrode assembly 102 and the second electrode assembly 104 (i.e., RF heating does not occur). When the RF circuit is closed, the RF generator 110 is able to cause an alternating electric field between the first electrode assembly 102 and the second electrode assembly 104 (i.e., RF heating does occur).

Controller 14 may include a user interface to receive a user input. In at least one example, the user input may be received via user input sensors 111 of the controller 14. Such user input sensors may include any one or combination of capacitive touch sensors, buttons, microphones for receiving voice commands, a mouse, keyboard, and a touch screen as mentioned above, for example.

In some examples, controller 14 may open the RF circuit responsive to receiving a user input to have the RF heating system in an off state. Additionally, the controller 14 may close the RF circuit responsive to receiving a user input to have the RF heating system in an on state.

In other examples, controller 14 may automatically open and close as a part of a continuous processing mode based on an output from environmental sensors such as temperature probe 108a, 108b, 108c and a user input received via user input sensors 111.

For example, in a continuous processing mode, multiple enclosures 106a, 106b, 106c may have agricultural plant products 114a, 114b, 114c that need to be RF heated, and these multiple enclosures 106a, 106b, 106c may be positioned on a conveyor belt 112. Thus, a controller may automatically actuate a conveyor belt 112 to move one of enclosures 106a, 106b, 106c into position between the first electrode assembly 102 and the second electrode assembly 104, close the RF circuit, heat the agricultural plant product within the enclosure moved between the first electrode assembly 102 and the second electrode assembly 104 to a threshold temperature in greater than a threshold amount of time, open the RF circuit, and then begin the process again. This cycle may continue for a set number of cycles. For example, a continuous mode may be carried out for a number of cycles that are indicated via user input to a controller 14 via user input sensors 111. In other examples, however, a continuous mode may be carried out for a number of cycles until detecting that there are no longer enclosures for processing.

Thus, via the RF heating system disclosed herein, a means of processing agricultural plant products in an efficient manner is provided. Further, compliance for *cannabis* farmers or farmers of other crops with state law regulations regarding yeast and mold populations may be provided. Additionally, an improvement in the consistency of agricultural plant product quality may be achieved, as this RF heating system both reduces the microbial load to acceptable limits and while avoiding degradation of the product. Furthermore, this RF heating system is especially advantageous, as is may provide a means for recovering crops that may be contaminated with high microbial loads.

Additionally, the RF heating system has the benefit of improving a drying process for agricultural plant products, such as *cannabis* or herbs. In particular, the RF heating system may shorten a drying time, improve control over moisture reduction, quickly reduce water activity, and aid in downstream post-harvest processing of the product. Thus, the RF heating system disclosed herein may aid in downstream processing by drying the agricultural plant product (e.g., *cannabis*, leafy vegetables, herbs, etc.) to a desired moisture content. Such a moisture content in a case of *cannabis* processing may be a moisture content that enables easy separation of "sugar leaves" from flowering buds of the *cannabis*, for example. Additionally, the RF heating system may aid in downstream processing through improving a quality and/or size of the agricultural plant product (e.g., *cannabis* buds, leafy vegetables, herbs, etc.) by not over drying the product, improving a product yield by reducing waste due to processing (mechanical trimming), and by reducing post-harvest production time and required labor.

Figure 2:
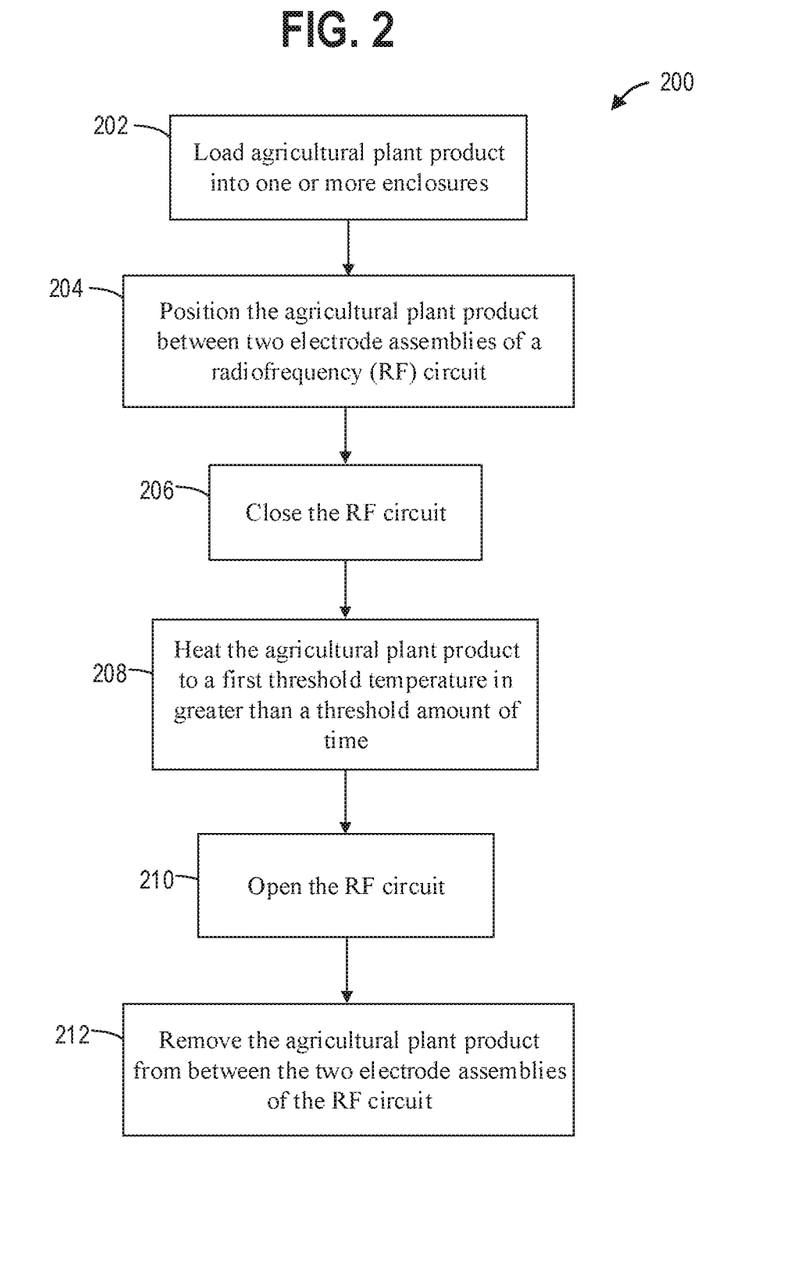
FIG. 2 shows a first example method for radiofrequency heating of an agricultural plant product according to at least one example of the present disclosure.

FIG. 2 shows a first example method 200 for radiofrequency heating of an agricultural plant product. In some examples, method 200 may be performed with an RF heating system such as described in FIG. 1. Thus, elements described in reference to FIG. 1 may also be referenced in the description of FIG. 2 using the same reference numerals.

The method described at FIG. 2 may be carried out continuously and automatically by non-transitory instructions of a controller in some examples. For example, the method described at FIG. 2 may be carried out by a controller 14 of the control system 13 described in reference to FIG. 1. However, in other examples, the method may not be automatically carried out by a controller and instead be carried out in batches.

The method may begin at step 202, where an agricultural plant product is loaded into one or more enclosures. In some examples, the agricultural plant product may be contained within an enclosure such as any of enclosures 106a, 106b, 106c. In some examples, a lid of the enclosure may be lightly closed in order to enable venting of steam, and in order to prevent a pressure build-up within enclosure during the RF heating. However, in other examples, the lid may be sealed. For example, if the enclosure includes other venting mechanisms (e.g., a mesh bottom 120, other openings 124 in the enclosure) the lid may be sealed as there is already a manner in which the steam may be vented out. It is noted that a shaping of such mesh or other openings may be varied. For example, rectangular slits, round holes, etc. may be possible. Further, it is noted that any combination of the features of the enclosures may be included in a single enclosure. As one example, an enclosure with the mesh or that has openings, may also have a lid. As another example, an enclosure that is a single piece solid tray may not have a lid. Other combinations may also be possible.

The enclosure may contain loosely packed agricultural plant product in order to ensure that the product is able to be efficiently heated. In some examples, a threshold mass amount of product for processing via the RF heating system may be predetermined. For example, between 1 kg and 5 kgs of an agricultural plant product, may be RF heated at a time. In addition to mass, a threshold height range of an agricultural plant product within the enclosure may be predetermined in order to approximate a density of agricultural plant product being processed at a time. For example, a height between 7.5 cm to 15 cm may be the threshold height range. In at least one example, the agricultural plant product may be *cannabis*. Additionally or alternatively, the agricultural plant product may include one or more of leafy vegetables and herbs.

Following loading the agricultural plant product into one or more enclosures at step 202, method 200 may include positioning the agricultural plant product between two electrode assemblies of a radiofrequency (RF) circuit at step 204 while the RF circuit is open. For example, agricultural plant product contained in one of the one or more enclosures may be positioned between two electrode assemblies of the RF circuit at step 204.

In some examples the agricultural plant product may be positioned between the two electrode assemblies of the RF circuit manually. However, in other examples, the agricultural plant product may be positioned between the two electrode assemblies of the RF circuit via a conveyor, such as conveyor belt 112.

As a part of positioning the enclosure containing agricultural plant product between the two electrode assemblies of the RF circuit at step 204, a position of the electrode assemblies may optionally be adjusted in order to ensure that a desired rate of heating may be achieved. However, in other examples, a position of the electrode assemblies may optionally be adjusted responsive to receiving a user input at step 206, as described later.

In examples where a position of the electrode assemblies relative to the agricultural plant product are adjusted as a part of positioning the enclosure between the two electrode assemblies at step 204, one or both of the electrode assemblies may be adjusted to ensure that the product reaches a threshold temperature in greater than a threshold amount of time. For example, a top electrode assembly may be adjusted such that the RF exposure time for the product to reach from an initial temperature to a final temperature (e.g., a maximum of 115 degrees Celsius) is not shorter than four minutes. A conveyor belt or a surface upon which the enclosure 106 rests when between the two electrode assemblies may also be adjusted at step 204. However, in some examples, neither the electrode assemblies nor the conveyor belt/surface for supporting the enclosure may be adjusted.

After the agricultural plant product has been positioned between two electrode assemblies of an RF circuit at step 204, the RF circuit may be closed. In some examples, the RF circuit may be closed responsive to a user input.

For example, in a batch mode for processing, the RF circuit may be closed responsive to a user input to turn on the RF heating system (i.e. close the RF circuit) for one cycle, where one cycle of positioning the agricultural plant product between the two electrode assemblies, closing the RF circuit, heating the plant agricultural plant product in greater than the threshold amount of time, and opening the RF circuit.

However, in other examples, the RF circuit may be closed automatically as a part of a continuous processing mode. For example, in a continuous processing mode, multiple enclosures, such as enclosures 106a, 106b, 106c may have agricultural plant product that needs to be RF heated, and these multiple enclosures 106a, 106b, 106c may be positioned on a conveyor belt, such as conveyor belt 112. Then responsive, to receiving a user input at a controller, such as controller 14, the controller may automatically actuate a conveyor belt to move one of the multiple enclosures 106a, 106b, 106c into position between the first electrode and the second electrode at step 204. The controller may also automatically adjust a positioning of the electrode assemblies relative to the agricultural plant product responsive to the user input via moving one or more of the first electrode assembly, the second electrode assembly, and the conveyor belt. For example, the controller may automatically adjust the positioning of the electrode assemblies relative to the agricultural plant product in order to ensure that the agricultural plant product is heated to a threshold temperature in greater than a threshold amount of time.

After moving one the agricultural product between the two electrode assemblies of the RF circuit via the conveyor in a continuous processing mode or manually in a batch processing mode, method 200 may include closing the RF circuit at step 206.

After closing the RF circuit at step 206, the agricultural plant product positioned between the two electrode assemblies may be heated to a first threshold temperature in greater than a threshold amount of time at step 208. For example, the RF circuit may be closed and the agricultural plant product may be heated as predetermined via a user input received at a controller of the RF device.

The user input received may select a particular agricultural plant product to be processed in some examples, and then a predetermined heating profile associated with the selected agricultural plant product may be carried out. Such a predetermined heating profile may include one or more of a first threshold temperature to which the agricultural plant product is to be heated, a minimum amount of time that may be used to heat the agricultural plant product to the first threshold temperature, a maximum rate of heating that may be used to heat the agricultural plant product to the first threshold temperature, and a second threshold temperature to which to cool the agricultural plant product following heating the agricultural plant product to the first threshold temperature, where the second threshold temperature is less than the first threshold temperature.

In other examples, however, the user input received may manual input of one or more of the first threshold temperature to which to heat the agricultural plant product, the minimum amount of time that may be used to heat the agricultural plant product to the first threshold temperature, a maximum rate of heating that may be used to heat the agricultural plant product to the first threshold temperature, the maximum rate of heating that may be used to heat the agricultural plant product to the first threshold temperature, and the second threshold temperature to which to cool the agricultural plant product following heating the agricultural plant product to the first threshold temperature.

Following heating, the agricultural plant product to the first threshold temperature in greater than the threshold amount of time at step 208 (i.e., heating the agricultural product to the threshold temperature at less than a threshold rate), step 210 of method 200 includes opening the RF circuit. In some examples, the RF circuit may be opened responsive to detecting that a temperature of the agricultural plant product has reached the first threshold temperature in greater than the threshold amount of time. For example, in some cases a temperature sensor may output the temperature of the agricultural plant product being heated to the controller, and the RF circuit may automatically be opened responsive to determining via the temperature sensor output that the agricultural plant product has been heated to the first threshold temperature in greater than the threshold amount of time.

Additionally or alternatively, other environmental sensor outputs may also be used to determine whether to open the RF circuit at step 210. For example, moisture sensors that may measure a moisture within an enclosure holding the agricultural plant product may be used to determine when to open the RF circuit at step 210. In some cases, the RF circuit may be opened at step 210 responsive to determining that the ambient moisture content within the enclosure is greater than a threshold moisture content, as this may indicate that the agricultural plant product has undergone sufficient steaming and that sufficient moisture has been removed from the agricultural plant product itself. Such sensors may be of any useful type. In some examples, the sensors may be those suitable for an RF environment.

In other examples, however, the RF circuit may be opened only based on greater than the threshold amount of time lapsing with the RF circuit closed.

Following step 210, step 212 of method 200 includes removing the agricultural plant product from between the two electrode assemblies of the RF circuit.

The RF heating process may then subsequently be carried out again.

Following step 208, in a continuous mode the cycle, as disclosed at steps 202 through 212, may be repeated automatically for a set number of cycles, moving a new enclosure containing agricultural plant product between the two electrode assemblies at each start of a cycle. For example, the continuous mode may be carried out for a number of cycles that are indicated via user input to a controller. In other examples, however, the continuous mode may be carried out for a number of cycles based on detecting that there are no longer enclosures for processing.

In another example, where the agricultural plant product is processed in a batch mode, after closure of the RF circuit at step 206, and heating the agricultural plant product at step 208 to a threshold temperature in greater than a threshold amount of time, method 200 may include opening the RF circuit at step 210, and then the agricultural plant product may be manually removed from between the two electrode assemblies of the RF circuit at step 212.

By heating the agricultural plant product to a threshold temperature in greater than a threshold amount of time, the agricultural plant product may be more evenly heated. In other words, by heating the agricultural plant product at less than a threshold rate, benefits in regards to more evenly heating the agricultural plant product may be realized. As one example, in a case where *cannabis* is the agricultural plant product, an RF frequency of 27.12 MHz±0.163 MHz may be used. However, other RF frequencies may be possible.

The first threshold amount of time in method 200 may be based on a predetermined heating rate and a desired temperature for the particular agricultural plant product being processed. For example, a threshold amount of time for RF heating *cannabis* may be set to greater than 4 minutes to reach a temperature of 75 to 95 degrees Celsius when heating the *cannabis* within the threshold range of heating rates.

In examples where *cannabis* is the agricultural plant product, a heating rate range of from 6.5 degrees Celsius per minute to 19.0 degrees Celsius per minute has been found to both enable uniform heating of the product as well as to reduce a moisture content to less than a threshold without damaging the *cannabis*.

The RF heating may be a part of a drying process for the agricultural plant product (e.g., leafy vegetables, herbs, *cannabis*, etc.) as well as a kill step. In particular, for the drying process of the *cannabis*, the *cannabis* buds are dried on the plant before the mechanical trimming of the buds. The moisture content of the buds prior to undergoing the drying process can range from 9 to 20%, and the inventors have found that the RF drying time may range between 1.5 minutes to 4 minutes in order to reach a target temperature range of about 55 to 66 degrees Celsius. Specifically, the inventors have found that during the RF heating, the RF penetrates through the air layers of the *cannabis* into the buds and drives the moisture from the inside of the bud out, expediting the drying process. However, in cases where the agricultural plant product may be a different plant product, other moisture contents may be desirable.

Following step 206, method 200 includes opening the RF circuit in order to stop RF heating of the agricultural plant product. Step 206 may occur automatically responsive to determining that the agricultural plant product has been heated to a threshold temperature. For example, a controller may receive an output from one or more temperature probes (e.g., temperature probe 108a, 108b, 108c) indicating a temperature of the agricultural plant product, and the controller may open the RF circuit responsive to an output from the temperature probe indicating that the temperature of the agricultural plant product has reached the threshold temperature.

If the enclosure has a lid, the lid may be automatically or manually removed or repositioned to be offset after opening the RF circuit at step 210 in order to allow the product to cool down and for further removal of moisture. In some examples, this cool down time may range from 10 to 15 minutes. In some examples, the cool down time may not be time based but rather based upon a temperature of the agricultural plant product decreasing below the second threshold temperature after the agricultural plant product has been heated to the first threshold temperature at step 208, the first threshold temperature being greater than the second threshold temperature. The cool down temperature may be monitored via the temperature probe, for example. In such examples, once the RF heated agricultural plant product has been cooled to less than a second temperature threshold, where the second temperature threshold is less than the first temperature thresholds, an alert may be generated. For example, an alert (e.g., auditory or visual) may be generated via the controller of the RF heating system, indicating that the agricultural plant product has been cooled to less than the second temperature threshold.

Further, in some examples where the agricultural plant product is moved via a conveyor belt instead of manually moved, the agricultural plant product may be moved downstream of the two electrode assemblies via the conveyor belt following heating the agricultural plant product to the first threshold temperature at step 208. In some cases, the agricultural plant product may first be cooled while positioned between the first and second electrode assemblies prior to moving the agricultural plant product downstream of the two electrode assemblies in order to reduce a length of the conveyor belt needed to process the agricultural plant product in a continuous manner. To aid in such a cooling process where the agricultural plant product remains positioned between the two electrodes assemblies during cooling, the doors of the RF circuit enclosure may be opened after the agricultural plant product is heated and maintained open while the agricultural plant product is cooled. In other examples, the agricultural plant product may be removed from the conveyor belt and allowed to cool naturally.

However, in other examples, rather than allowing the agricultural plant product to cool down while positioned between the two electrode assemblies, the agricultural plant product may be immediately moved downstream of the two electrode assemblies after the agricultural plant product has been heated to the threshold temperature at step 208. In other examples, the agricultural plant product may be removed from the conveyor belt and allowed to cool at room temperature.

Such immediate conveying the agricultural plant product downstream of the two electrode assemblies after heating the agricultural plant product to the temperature threshold at step 208 may include immediately opening both doors of the RF circuit enclosure following heating of the agricultural plant product to the threshold temperature, and operating the conveyor belt to move the agricultural plant product that has been heated downstream of the RF circuit enclosure while also conveying any upstream agricultural plant product to be positioned between the two RF electrode circuit assemblies. Immediately moving the agricultural plant product after such agricultural plant product has been heated to the threshold temperature may advantageously allow agricultural plant product to be more quickly processed. In some examples, the agricultural plant product may be removed from the conveyor belt based system and allowed to cool naturally.

Figure 3:
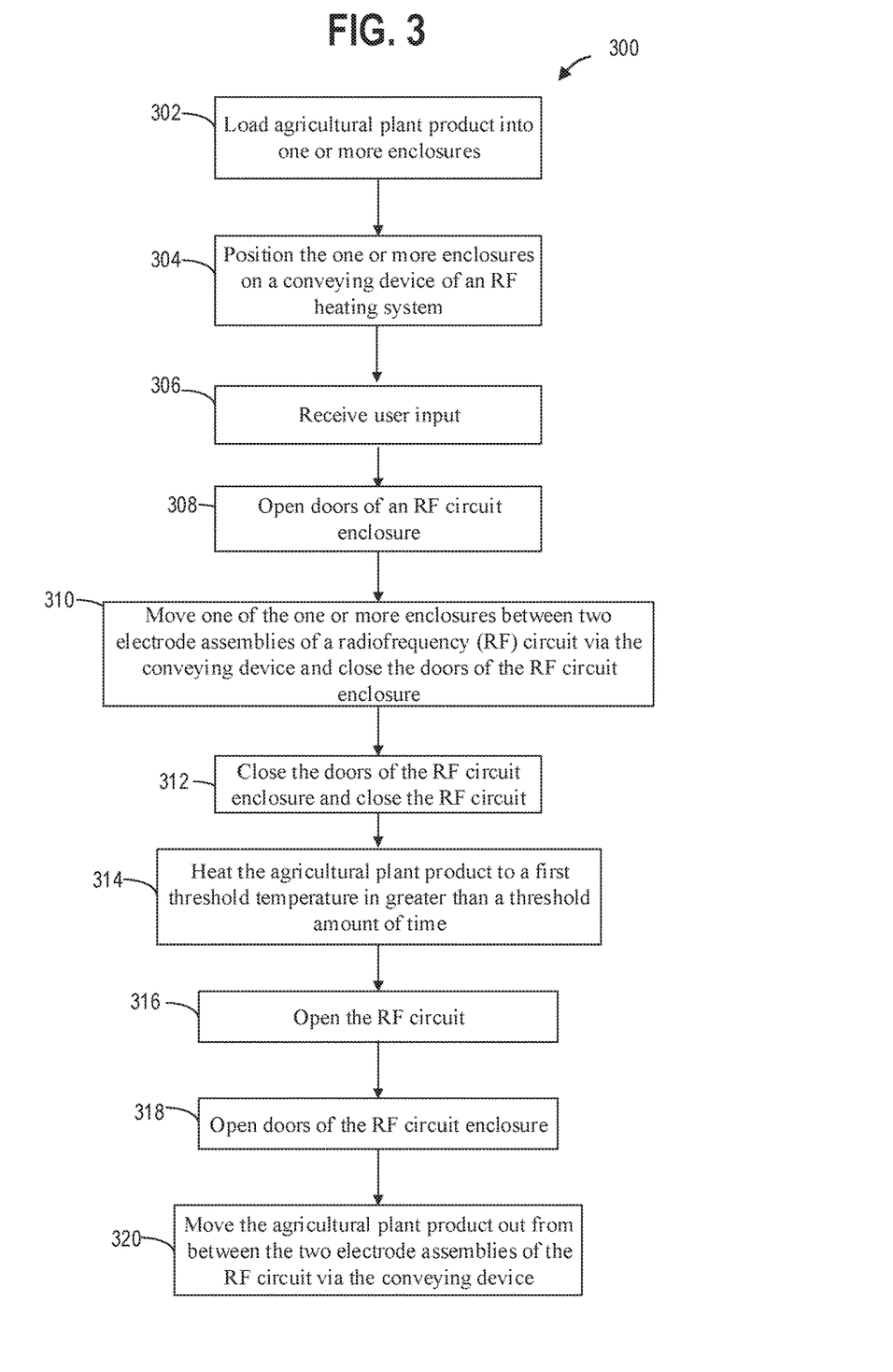
FIG. 3 shows a second example method for radiofrequency heating of an agricultural plant product according to at least one example of the present disclosure.

Turning now to FIG. 3, FIG. 3 shows a flow chart of a second example method 300 for processing agricultural plant products according to at least one example of the present disclosure. In some examples, method 300 may be performed with an RF heating system such as described in FIG. 1. Thus, elements described in reference to FIG. 1 may also be referenced in the description of FIG. 3.

Method 300 begins at step 302 where agricultural plant product is loaded into one or more enclosures. For example, agricultural plant product may be loaded into any one of the enclosures previously described herein.

Following loading the agricultural plant product into the one or more enclosures at step 302, method 300 includes positioning the one or more enclosures on a conveying device of an RF heating system at step 304. The conveying device may be a conveying belt, such as conveyor belt 112, for example. The one or more enclosures may all be positioned on the conveying device upstream of RF electrode assemblies.

Following positioning the one or more enclosures on the conveying device of the RF heating system upstream of the RF electrode assemblies at step 304, method 300 may include receiving a user input at step 306. The user input may be received via a controller, such as controller 14. The user input received may provide a command to perform continuous RF heat processing.

In at least one example, the user input may include selecting a particular agricultural plant product to be heated via RF heat processing, such that a predetermined heating profile for the selected agricultural plant product may be carried out. Such predetermined heating profiles may include the threshold temperature to which the agricultural plant product needs to be heated as well as a minimum threshold amount of time that the heating process needs to take place over.

Put another way, the predetermined heating profiles may include the threshold temperature to which the agricultural plant product needs to be heated as well as a maximum rate of heating that may be used for heating the agricultural plant product. In at least one example, the predetermined heating profile may also include a second threshold temperature that is lower than the first threshold temperature to which the agricultural plant product may be cooled following heating the agricultural plant product to the first threshold temperature.

In other examples, the user input may include a first threshold temperature that the agricultural plant product is to be heated to as well as a minimum length of time that may be used to heat the agricultural plant product to the first threshold temperature. Put another way, the user input may include manual input of the first threshold temperature to which the agricultural plant product is to be heated as well as a maximum rate at which the agricultural plant product is to be heated. Additionally or alternatively, the user input may also manually provide a second threshold temperature to which the agricultural plant product is to be cooled following heating of the agricultural product to the first threshold temperature, where the second threshold temperature is lower than the first threshold temperature. Such manual entry of the heating parameters is in contrast to the user input selecting an agricultural plant product to be RF heated that already has a predetermined heating profile.

It is noted that in cases where manual entry of heating parameters are entered, such heating parameters may be saved and associated with an agricultural plant product for subsequent use. For example, following manual entry and saving of heating parameters to associate the manually entered heating parameters with a particular agricultural plant product, during subsequent use of the RF heating system upon which the heating parameters were saved, a user may select the agricultural plant product associated with the saved heating parameters rather having to re-enter the heating parameters.

Moreover, in at least one example, it may be desirable to include multiple RF heating profiles for a same agricultural plant product. For example, it may be desirable to have a drying RF heating process for an agricultural plant product as well as a kill step only RF heating profile for the same agricultural plant product. Thus, reference to selecting an agricultural plant product for RF heating may also refer to selection of a particular RF heating process for an agricultural plant product, in at least one example.

Following receiving the user input at step 306, method 300 may comprise automatically opening the doors of an RF circuit enclosure (if they are not already opened) at step 308, and then moving one of the one or more enclosures that are positioned on the conveyor belt upstream the RF electrode assemblies to be positioned between the two electrode assemblies of an RF circuit via the conveying device at step 310 while the RF circuit is open.

Optionally, step 310 may also include adjusting one or more of the first electrode assembly, the second electrode assembly, and a position of the conveyor belt to position the agricultural plant product relative to the first and second electrode assemblies to ensure that the agricultural plant product is heated to the first threshold temperature in greater than the threshold amount of time.

Following step 310, step 312 includes closing the doors of the RF circuit enclosure and closing the RF circuit. Closing the RF circuit commences heating of the agricultural plant product positioned between the RF electrode assemblies.

Following step 312, step 314 of method 300 includes heating the agricultural plant product to the first threshold temperature in greater than a threshold amount of time. The first threshold temperature and the threshold amount of time at step 314 may be based on the user input received at step 306 of method 300, for example. In other words, the agricultural plant product may be heated to the first threshold temperature at less than a threshold rate at step 314.

Following step 314, step 316 may include opening the RF circuit. The RF circuit may be opened responsive to differentiating that the agricultural plant product temperature is greater than the first threshold temperature. The agricultural plant product may be differentiated as having a temperature greater than the first threshold temperature responsive to receiving an output from a temperature probe, for example. In other examples, however, the RF circuit may be opened after carrying out the heating profile based on the user input at step 306, regardless of output from a temperature sensor.

After the RF circuit is opened at step 316, the doors of the RF circuit enclosure may be opened at step 318. In some examples, the doors of the RF circuit enclosure may be immediately opened at step 318 following the agricultural plant product being heated to the first threshold temperature in greater than the threshold amount of time. Such immediate opening of the doors may help to cool the agricultural plant product that was heated to a second threshold temperature, for example. Further, immediate opening of the doors may enable the agricultural plant product that was heated to more quickly be moved out from between the two electrode assemblies such that more agricultural plant product may be moved between the two electrode assemblies for heating. In further examples, the agricultural plant product may be removed from the RF circuit enclosure and allowed to cool at room temperature.

However, in other examples, the doors of the RF circuit enclosure may be maintained in a closed state following heating of the agricultural plant product to extend the heating process.

Following step 318, step 320 of method 300 may include maintaining the doors of the RF circuit enclosure open and moving the agricultural plant product out from between the two electrode assemblies of the RF circuit via the conveying device. In particular, the agricultural plant product may be moved out from between the two electrode assemblies of the RF circuit to downstream the two electrode assemblies of the RF circuit. As the agricultural plant product that was heated to the first threshold temperature is moved out from between the two electrode assemblies, agricultural plant product that may be on the conveyor upstream of the two electrode assemblies, may be moved to be positioned between the two electrode assemblies. Such agricultural plant product that was positioned on the conveyor upstream of the two electrode assemblies may be contained in an enclosure, for example.

Additionally, in examples where agricultural plant product that was heated may be contained in an enclosure, a lid of the enclosure may be removed or offset to aid in cooling the agricultural plant product to a second threshold temperature that is less than the first threshold temperature. Additionally, in at least one example, an alert may be generated when the agricultural plant product is cooled to the second temperature, as described in relation to method 200.

Figure 4:
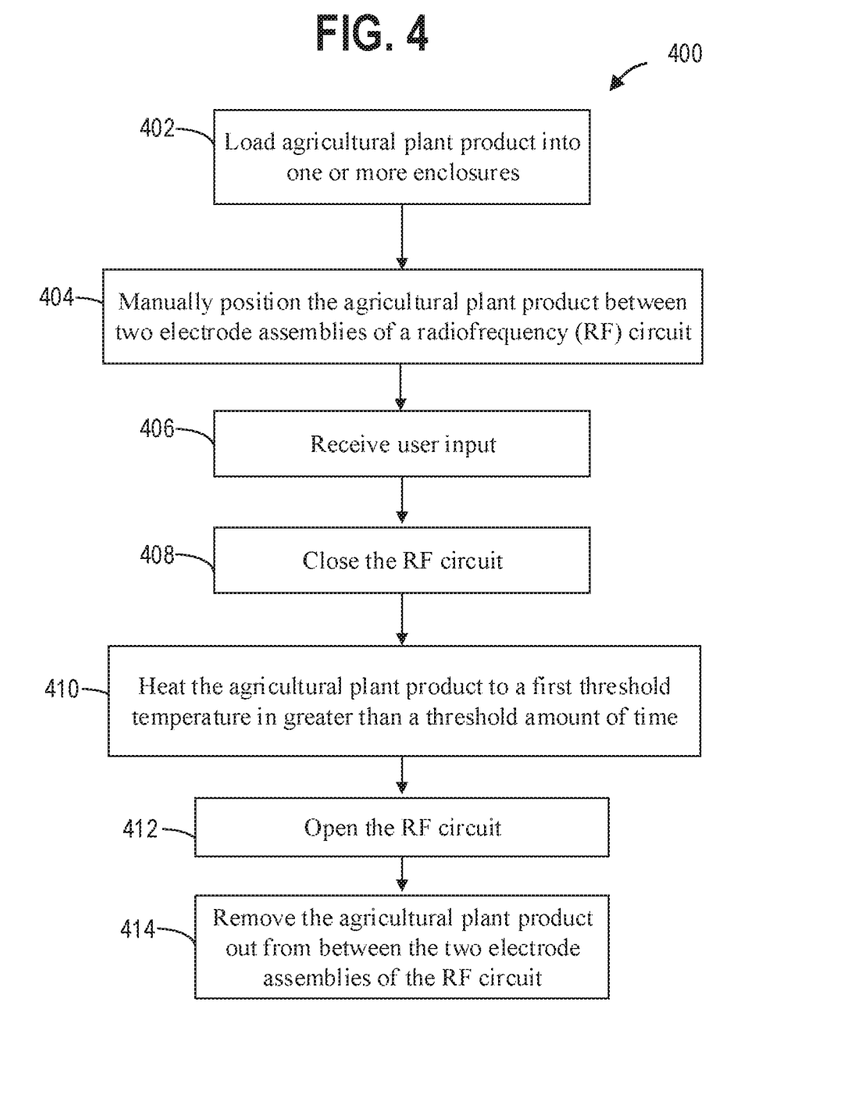
FIG. 4 shows a third example method for radiofrequency heating of an agricultural plant product according to at least one example of the present disclosure.

Turning now to FIG. 4, FIG. 4 shows a flow chart of a third example method 400. Method 400 may be carried via the RF heating system as described at FIG. 1, in at least one example.

Method 400 may begin at step 402, which includes loading agricultural plant product into one or more enclosures. The one or more enclosures may include any one or combination of the features of the enclosures described above, for example.

Following loading the agricultural plant product into the one or more enclosures, the agricultural plant product may be manually positioned between two electrode assemblies of a radiofrequency (RF) circuit at step 404 while the RF circuit is open. For example, the agricultural plant product may be manually positioned between the two electrode assemblies of the RF circuit by opening at least one door of an RF circuit enclosure and placing the agricultural plant product (e.g., agricultural plant product contained in an enclosure) on a surface between the two electrode assemblies. Once the agricultural plant product is positioned between the two electrode assemblies, all doors of the RF circuit enclosure may be closed at step 404.

Following manually positioning the agricultural plant product between the two electrode assemblies at step 404, method 400 may include receiving a user input at step 406. For example, the user input may be received at a controller of the RF heating system. The user input may include selection of an agricultural plant product or manual entry of heating parameters. For example, any one or combination of the user inputs described above in relation to step 306 of method 300 may be received at step 406 of method 400.

Once the user input is received at step 406, the RF circuit may be closed at step 408. Optionally, step 408 may also include adjusting one or more of the first electrode assembly, the second electrode assembly, and a position of the surface (e.g., a height of the surface) between the electrode assemblies upon which the agricultural plant product is positioned. Such adjusting may be to position the agricultural plant product relative to the first and second electrode assemblies to ensure that the agricultural plant product is heated to a first threshold temperature in greater than a threshold amount of time.

At step 410, the agricultural plant product may be heated to the first threshold temperature in greater than the threshold amount of time, and may include details as described in relation to step 314 of method 300.

Following heating the agricultural plant product to the first threshold temperature in greater than the threshold amount of time at step 410, step 412 may include opening the RF circuit. Step 412 may details as described in relation to step 316 of method 300.

Following step 412, method 400 includes removing the agricultural plant product out from between the two electrode assemblies of the RF circuit. For example, removing the agricultural plant product out from between the two electrode assemblies may include opening a door of the RF circuit enclosure and manually removing the agricultural plant product that was heated at step 410. In some examples, a lid of an enclosure containing the agricultural plant product may then be removed or offset to expedite cooling of the agricultural plant product to below a second threshold temperature. Additionally, in at least one example, an alert may be generated when the agricultural plant product is cooled to the second temperature, as described in relation to method 200.

Thus, provided is a system and a method for RF heating of an agricultural plant product such as *cannabis*, leafy vegetables, or herbs. A first example method may include positioning an agricultural plant product between two electrode assemblies of a radiofrequency (RF) circuit, closing the RF circuit, and heating the agricultural plant product to a threshold temperature in greater than a threshold amount of time. A second example of the method, which may optionally include the first method may include adjusting a distance between one of the two electrode assemblies and the agricultural plant product. Further, a fourth example method, which may optionally include any of the preceding methods, may include opening the RF circuit responsive to the agricultural plant product reaching the threshold temperature.

Thus, via the system and methods described herein, a manner for achieving a post-harvest kill step may be provided to reduce yeast and mold population with minimal negative impact on the chemical composition, organic, and organoleptic composition of the agricultural plant product (e.g., *cannabis*). Additionally, an improved approach for quickly reducing a moisture content, water activity, and product optimization for downstream post-harvest processing (e.g., mechanical trimming) may be realized.

It will be appreciated that the configurations and/or approaches described herein are exemplary in nature, and that these specific embodiments or examples are not to be considered in a limiting sense, because numerous variations are possible. The subject matter of the present disclosure includes all novel and nonobvious combinations and subcombinations of the various features, functions, acts, and/or properties disclosed herein, as well as any and all equivalents thereof.

The invention claimed is:

1. A method, comprising:
positioning an enclosure containing an agricultural plant product between two electrode assemblies of a radiofrequency (RF) circuit, wherein the agricultural plant product is *cannabis*;
closing the RF circuit;
subjecting the *cannabis* to RF waves via the closed RF circuit for at least four minutes; and
heating and drying the *cannabis* via the RF waves, the *cannabis* heated to a final temperature ranging from 75 degrees Celsius to 115 degrees Celsius via the RF waves.

2. The method of claim 1, wherein the enclosure is a moving enclosure, and wherein medicinal properties of the *cannabis* are maintained following the heating and the drying of the *cannabis*.

3. The method of claim 1, further comprising differentiating that the *cannabis* has reached a threshold temperature, and then automatically opening the RF circuit via a controller.

4. The method of claim 3, where a temperature of the *cannabis* is monitored via at least one temperature probe positioned within the enclosure that provides an output to the controller.

5. The method of claim 1, wherein a frequency of the RF waves is 27.12 MHz±0.163.

6. The method of claim 1, wherein the enclosure comprises vents.

7. The method of claim 1, wherein the enclosure is a tray comprising polycarbonate, the polycarbonate tray including a fitted lid.

8. The method of claim 7, wherein a bottom of the polycarbonate tray comprises a mesh.

9. The method of claim 1, wherein the *cannabis* is dried via vaporization of water within the *cannabis*, and wherein the *cannabis* is dried without adding any moisture to the *cannabis* from a foreign source.

10. The method of claim 1, further comprising heating the *cannabis* with a heating rate that is less than 19.0 degrees Celsius per minute via the RF waves.

11. A method of treating an agricultural product, comprising:
subjecting the agricultural product to radiofrequency (RF) waves, wherein the agricultural product is *cannabis*;
heating the *cannabis* to a final temperature ranging from 75 degrees Celsius to 115 degrees Celsius via the RF waves at a heating rate that is less than 19.0 degrees Celsius per minute; and
via subjecting the *cannabis* to the RF waves, reducing a microbial load of the *cannabis* to an acceptable limit while avoiding degradation of a chemical composition of the *cannabis*.

12. The method of claim 11, wherein the chemical composition of the *cannabis* includes THC.

13. The method of claim 11, wherein the chemical composition of the *cannabis* includes color chemicals and terpenes.

14. The method of claim 11, wherein the *cannabis* is subjected to the RF waves for at least four minutes, and wherein the heating rate is greater than 6.5 degrees Celsius per minute.

15. The method of claim 11, further comprising drying the *cannabis* via the RF waves.

16. A method, comprising:
loading a leafy agricultural plant product into an enclosure;
positioning the enclosure containing the leafy agricultural plant product between two electrode assemblies of a radiofrequency (RF) circuit;
closing the RF circuit;
subjecting the leafy agricultural plant product to RF waves via the closed RF circuit; and
heating the leafy agricultural plant product via the RF waves to a final temperature ranging from 75 degrees Celsius to 115 degrees Celsius, the leafy agricultural plant product heated at a heating rate that is less than 19.0 degrees Celsius per minute.

17. The method of claim 16, wherein the leafy agricultural plant product is *cannabis*.

18. The method of claim 16, wherein a frequency of the RF waves is 27.12 MHz±0.163 MHz.

19. The method of claim 16, wherein the heating rate is greater than 6.5 degrees Celsius per minute, and wherein the enclosure is made of polycarbonate.

20. The method of claim 19, further comprising drying the *cannabis* contained within the enclosure via the RF waves.

* * * * *

UNITED STATES PATENT AND TRADEMARK OFFICE
CERTIFICATE OF CORRECTION

PATENT NO. : 10,517,308 B2
APPLICATION NO. : 15/784003
DATED : December 31, 2019
INVENTOR(S) : Andre Rehkopf Page 1 of 1

It is certified that error appears in the above-identified patent and that said Letters Patent is hereby corrected as shown below:

In Column 1, under the section entitled SUMMARY, Lines 49-53:
Correct "$\lambda=2\pi f/c$" to read "$\lambda$"

Signed and Sealed this
Twenty-sixth Day of May, 2020

Andrei Iancu
*Director of the United States Patent and Trademark Office*